US008881726B2

(12) United States Patent
Wyatt

(10) Patent No.: US 8,881,726 B2
(45) Date of Patent: Nov. 11, 2014

(54) METHOD OF RELIEVING PAIN ASSOCIATED WITH FRACTURED RIBS

(71) Applicant: William T. Wyatt, Reform, AL (US)

(72) Inventor: William T. Wyatt, Reform, AL (US)

(*) Notice: Subject to any disclaimer, the term of this patent is extended or adjusted under 35 U.S.C. 154(b) by 0 days.

(21) Appl. No.: 13/914,041

(22) Filed: Jun. 10, 2013

(65) Prior Publication Data

US 2013/0269691 A1   Oct. 17, 2013

Related U.S. Application Data

(63) Continuation-in-part of application No. 13/465,759, filed on May 7, 2012, now abandoned.

(60) Provisional application No. 61/580,483, filed on Dec. 27, 2011.

(51) Int. Cl.
*A61M 16/06* (2006.01)
*A61M 16/00* (2006.01)
*A61M 16/08* (2006.01)

(52) U.S. Cl.
CPC ....... *A61M 16/0057* (2013.01); *A61M 16/0066* (2013.01); *A61M 16/0875* (2013.01); *A61M 16/00* (2013.01); *A61M 16/0666* (2013.01)
USPC ............ 128/204.21; 128/204.18; 128/205.25; 128/206.21; 128/200.24

(58) Field of Classification Search
CPC .... A61G 10/026; A61M 11/00; A61M 15/00; A61M 16/00; A61M 16/06; A61M 16/1075; A61M 16/16; A61M 2016/0006; A61M 2016/0039; A61M 2021/0022; A61M 21/02; A61M 2202/0208; A62B 31/00; A62B 9/003
USPC ............ 128/200.24, 201.22–201.29, 202.11, 128/202.12, 205.26; 601/6, 11, 14, 601/148–152, 23; 602/75, 13, 27; 600/21, 600/22
See application file for complete search history.

(56) References Cited

U.S. PATENT DOCUMENTS

| 4,305,387 | A |   | 12/1981 | Reist-Kundig et al. |
|---|---|---|---|---|
| 4,870,963 | A |   | 10/1989 | Carter |
| 5,109,837 | A | * | 5/1992 | Gamow ................... 128/202.12 |
| 5,133,339 | A |   | 7/1992 | Whalen et al. |
| 5,327,904 | A |   | 7/1994 | Hannum |
| 5,664,562 | A |   | 9/1997 | Bourdon |
| 6,123,071 | A |   | 9/2000 | Berthon-Jones et al. |
| 6,532,960 | B1 |   | 3/2003 | Yurko |

(Continued)

OTHER PUBLICATIONS

Dutta et al., Pneumatic stabilization of iatrogenic flail chest with CPAP: a case report. Acta Anaesthesiologica Belgica, 2010, 61(1), pp. 25-28.

*Primary Examiner* — Annette Dixon
(74) *Attorney, Agent, or Firm* — Bush Intellectual Property Law; Kenneth M. Bush

(57) ABSTRACT

A method of relieving pain resulting from breathing in a patient with fractured ribs, wherein the pain interrupts the sleeping of the patient. A positive airway pressure machine is attached to the nose or nose and mouth of the patient. The patient turns the machine on to produce a positive airway pressure in the airways of the lungs and adjusts the positive airway pressure to a level where the patient feels that the pain is reduced or eliminated. The method allows a patient with fractured ribs to sleep comfortably without the pain associated with breathing in and out, and without interruption of sleep. The method also promotes the healing and recovery of the fractured ribs.

2 Claims, 1 Drawing Sheet

(56) References Cited

U.S. PATENT DOCUMENTS

| | | |
|---|---|---|
| 7,562,659 B2 | 7/2009 | Matarasso |
| 7,810,496 B2 | 10/2010 | Estes et al. |
| 7,879,823 B2 | 2/2011 | Seiberg et al. |
| 7,931,023 B2 | 4/2011 | Berthon-Jones et al. |
| 2005/0279367 A1 | 12/2005 | Klemperer |
| 2007/0283958 A1 | 12/2007 | Naghavi |
| 2008/0216831 A1 | 9/2008 | McGinnis et al. |
| 2009/0194108 A1 | 8/2009 | Newman, Jr. |
| 2010/0026499 A1 | 2/2010 | Lamb |
| 2010/0170513 A1 | 7/2010 | Bowditch et al. |

* cited by examiner

METHOD OF RELIEVING PAIN ASSOCIATED WITH FRACTURED RIBS

CROSS-REFERENCE TO RELATED APPLICATIONS

This application claims priority of U.S. Provisional Application Ser. No. 61/580,483 filed Dec. 27, 2011 and of U.S. patent application Ser. No. 13/465,759 filed May 7, 2012, the disclosures of which are incorporated herein by reference.

FIELD OF THE INVENTION

The present invention relates to the field of positive airway pressure machines and, more particularly, to a method of relieving pain in patients with broken ribs, wherein the pain is caused by the patient breathing in and out. The pain is relieved with externally applied continuous positive airway pressure delivered to the lungs of the patient using a positive airway pressure machine.

BACKGROUND OF THE INVENTION

Whenever ribs are fractured, either accidentally or through a medical procedure, there is little that can be done to prevent or relieve the pain associated with the recovery and healing of the ribs, or to promote the healing of the fractured ribs. Applying tape to the thorax to stabilize the ribs is not recommended because it is associated with the occurrence of pneumonia. Patients receive pain medication and are instructed to sleep in a recliner and are advised that it will take three to six months for the pain to subside. A relatively serious problem is that the pain interferes with a patient's ability to get an adequate amount of sleep as a result of the pain interrupting sleep. The pain is usually caused by the movement of the fractured portion of the ribs during breathing in and out. The interruption of sleep may interfere with the healing process of the fractured ribs. What is needed is a method for relieving pain caused by breathing, particularly during sleeping to prevent the interruption of sleep.

SUMMARY OF THE INVENTION

The present invention provides a method of relieving pain in a patient with fractured ribs wherein the pain is produced by the patient breathing in and out and the pain interrupts the patient's sleeping. A positive airway pressure machine is provided having a hose with a face mask assembly or nostril piece wherein the hose delivers positive air flow pressure from the positive airway pressure machine to the face mask assembly or to the nostril piece. The positive airway pressure machine has an air flow pressure control device. The face mask assembly or the nostril piece is attached to the face or nose of the patient. The patient turns on the positive airway pressure machine to produce a positive airway pressure in the airway or airways of the lungs of the patient. The patient adjusts the positive airway pressure produced by the positive airway pressure machine by manually adjusting the air flow pressure control device to a level where the patient feels that the pain produced by breathing in and out is reduced or eliminated. The interruption of sleep caused by the patient breathing in and out is thereby prevented, and the healing of the fractured ribs of the patient is thereby accelerated. The method is used until at least no movement of the fractured portion of the ribs is felt by the patient during normal breathing when the patient is not using the positive airway pressure machine. The positive airway pressure machine may be non-ventilating.

An advantage of the invention is a simple and safe method for relieving pain in a patient with fractured ribs that occurs during breathing and that is associated with movement of the fractured portion of the ribs.

Another advantage is a method which promotes the healing and recovery of fractured ribs.

Another advantage is a method which allows a patient with fractured ribs to sleep comfortably without the pain associated with breathing and without the interruption of sleep that would otherwise occur with in and out breathing of the patient.

Another advantage is a method which helps prevent pneumonia in the patient by producing a positive pressure in the lungs and which helps prevent the lungs from collapsing.

DETAILED DESCRIPTION OF THE INVENTION

While the following description details the preferred embodiments of the present invention, it is to be understood that the invention is not limited in its application to the details of the method described herein, since the invention is capable of other embodiments and of being practiced in various ways.

Figure 1A:
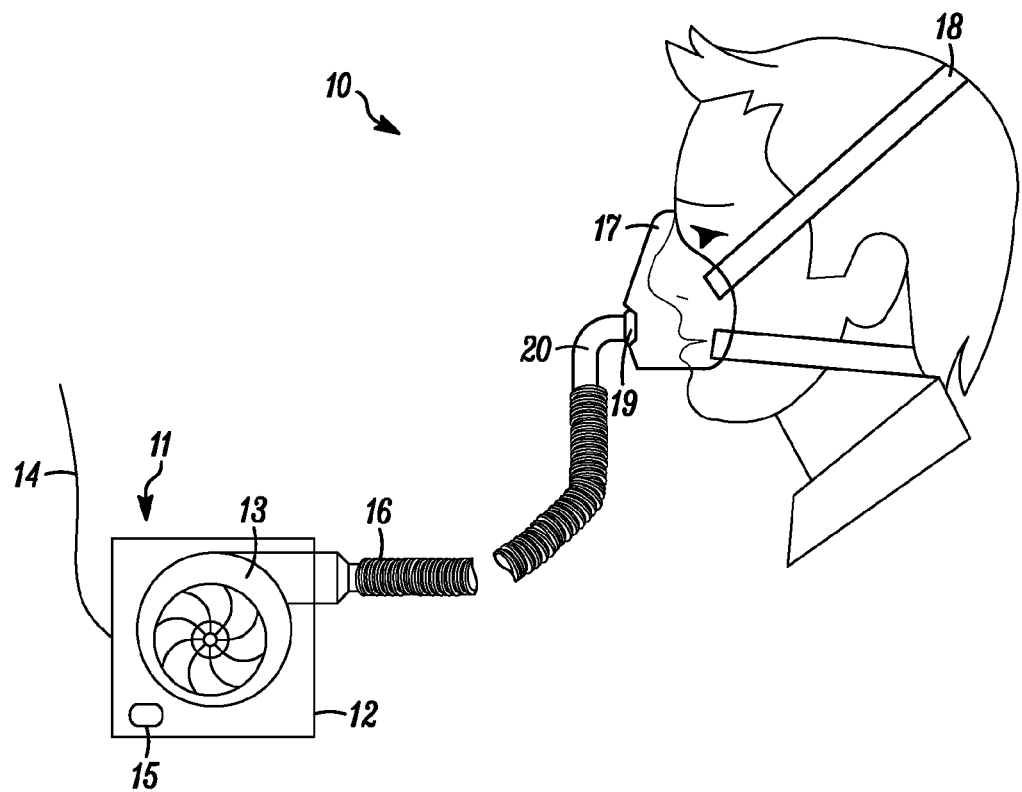
FIG. 1a shows a typical positive airway pressure system having a positive airway pressure machine connected to a face mask assembly.
Figure 1B:
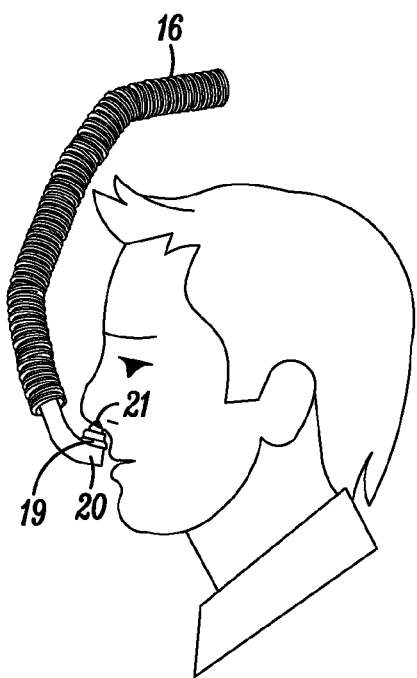
FIG. 1b shows an alternate nostril assembly that can be used with the positive airway pressure machine.

The method of the present invention uses a positive airway pressure machine, preferably a continuous positive airway pressure (CPAP) or bi-level positive airway pressure (BPAP) machine, or known variations thereof. A description of a typical positive airway pressure machine that can be used in the method of this invention is shown in FIGS. 1a and 1b. FIG. 1a shows a typical positive airway pressure system 10 having a positive airway pressure machine 11. The positive airway pressure machine 11 has a housing 12 with an airflow pressure generator 13 contained therein, a power cord 14, and an air flow pressure control device 15. The air flow pressure control device 15 can be any kind of knob, button, lever, key, or the like which are well known in the art. Air flow pressure can be increased or decreased by a health care practitioner or the patient using the air flow pressure control device 15 by methods well known in the art. The positive airway pressure machine 11 also has a hose 16 to deliver a flow of air to a user. One end of the hose 16 is attached to the positive airway pressure machine 11 and the opposite end of the hose 16 has a short tube 20 attached thereto. The short tube 20 is attached to a face mask assembly 17 which can be held over the nose and mouth of a user by straps 18. FIG. 1b illustrates that the short tube 20 can alternatively have a nostril piece 21 which fits into the nose of a user. The short tube 20 may also have a continuous venting arrangement 19, well known in the art, which allows for gases in the exhaled air flow of the user to be diverted from the incoming air flow to prevent re-breathing of the exhaled gases.

These positive airway pressure machines are designed to maintain a positive pressure in the airway of the lung to prevent sleep apnea. During sleep apnea the airway is prone to narrowing or collapsing. The positive air pressure keeps the airway open and prevents the occurrence of obstructive sleep apnea syndrome. However, U.S. Pat. No. 7,810,496 teaches that the surplus inspiratory positive airway pressure at the end of inspiration that occurs with a non-ventilating BPAP machine leads to uncomfortable and potentially harmful hyperinflation of patient's lungs. This patent further teaches that the administration of expiratory positive airway air pressure throughout the expiratory cycle with the BPAP machine undesirably contributes to the breathing work that a patient must perform during exhalation. These effects produced by a non-ventilating BPAP machine suggest that this machine would not be useful for relieving the pain associated with breathing in a patient with broken ribs, and would probably exacerbate the pain and delay the process of healing of, and the recovery from, the broken ribs.

The method of the present invention uses positive airway pressure devices known in the art. The device may typically include a drive system for generating a pressurized air stream variably at a volume and pressure as desired, and may include a delivery system of fittings, tubing/hoses, and masks in order to deliver the pressurized air into the breathing system of a patient. The device may include various electrical and electronic control systems in order to turn the machine on and off, control the air pressure or motor speed, and the like. Other systems may be incorporated to accommodate the valving of air flows to and from the lungs of a patient. The power system for the device includes wall power, converted DC power from an AC wall outlet through a DC power supply, DC power from an automobile outlet through a DC power supply, a battery, or the like.

The method of the present invention comprises 1) providing a positive airway pressure machine 11 having a hose 16 with a face mask assembly 17 or nostril piece 21 wherein the hose delivers positive air flow pressure from the positive airway pressure machine 11 to the face mask assembly 17 or the nostril piece 21; 2) attaching the face mask assembly 17 or nostril piece 21 to the face or nose of a patient having fractured ribs so that a positive air flow pressure is produced in the airway and lungs of the patient; 3) turning on the positive airway pressure machine 11 and adjusting positive airway pressure, by adjusting the air pressure control device 15, to a level where the patient feels that the pain caused by breathing in and out is reduced or eliminated and, if desired, adjusting positive airway pressure to a level where the patient feels that the movement of the fractured ribs caused by breathing in and out is reduced or eliminated; and 4) using the positive airway pressure machine 11, preferably for at least two days, or until the patient does not feel the movement of the fractured ribs during normal breathing in and out when the patient is not using the positive airway pressure machine 11.

The positive airway pressure machine can produce continuous or intermittent air pressure in the airway(s) of the patient at levels from 4 to 30 cm $H_2O$. The patient applies the mask or nostril piece to his or her face or nose and adjusts the air pressure produced by the positive airway pressure machine, by adjusting the air pressure control device, to a level where the pain associated with breathing is reduced as desired. Anyone can assist the patient, if desired, in adjusting the positive air pressure. Preferably, however, the patient can adjust the positive airway pressure by himself or herself. The positive airway pressure device can be constructed as a small, portable device that can be powered by any power source known in the art.

EXAMPLE

A patient had fallen and complained that his ribs may have been broken. X-ray examination revealed that the number nine and ten ribs on the left side were broken. The patient received standard pain medication and was instructed to sleep in a recliner chair. At night the patient attempted to sleep in a recliner chair. With each breath in and out there was a sharp pain in his left side which interrupted his sleeping and prevented him from sleeping. He could feel his broken ribs moving during breathing in and out. The patient then went to his bed to lie down and sleep, but experienced the same pain during breathing. The patient could feel that the pain was associated with movement of the broken ribs. His sleeping was interrupted and he was not able to sleep. The patient had previously, prior to his fall and resulting broken ribs, been prescribed a positive airway pressure device (BPAP) for the treatment of sleep apnea. Later in the night the patient attached his BPAP machine to prevent any sleep apnea in the event he was able to fall asleep. When the patient turned on the device, it completely relieved the pain associated with breathing as the patient adjusted the pressure to 16 cm of water. The patient then shut off the BPAP machine and the pain associated with breathing returned immediately. The patient then repeated this process six more times with the same results. The patient then left the BPAP machine on for the rest of the night and was able to sleep without any of the prior pain or discomfort and without the prior interruption of his sleep related to his broken ribs. For the next five days the patient used the BPAP machine set at his selected positive airway pressure which prevented pain during breathing in and out. He also used the BPAP machine at night while sleeping and the interruption of sleep was prevented by use of the BPAP machine as described above. After five days, the patient could no longer feel the broken portion of his ribs moving during normal breathing when not using the BPAP machine. Thereafter, he was able to resume his normal work activities, did not require the further use of the BPAP machine to prevent pain during breathing or to prevent interruption of sleep, and has had no such pain since.

The mechanism of action whereby continuous positive airway pressure relieves pain during breathing in patients with broken ribs is unknown. It may be that the continuous fixed positive airway pressure in the lungs created by the device produced an internal splinting of the chest wall resulting in pain relief and accelerated healing and knitting of the broken ribs. The continuous positive airway pressure in the lung may also produce alveolar recruitment thereby preventing the atelectasis and pneumonia that might result as a complication of fractured ribs. Any suitable type of positive pressure airway device known in the art may be used in the method of the present invention. The use of the positive pressure airway device may be needed for only one or two days to promote healing of the ribs sufficiently so that the device is no longer required for the duration of the healing period.

While the invention has been shown and described in some detail with reference to specific exemplary embodiments, there is no intention that the invention be limited to such detail. On the contrary, the invention is intended to include any alternative or equivalent embodiments that fall within the spirit and scope of the invention as described herein.

With respect to the above description then, it is to be realized that the optimum dimensional relationships for devices used in the method of the invention, to include variations in size, materials, shape, form, function and manner of operation, assembly and use, are deemed readily apparent and obvious to one skilled in the art, and all equivalent relationships to those described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact method and operation described, and accordingly, all suitable modifications and equivalents may be resorted to, falling within the scope of the invention.

The invention claimed is:

1. A method of relieving pain in a patient having one or more fractured ribs, wherein the pain is produced by the patient breathing in and out and wherein the pain interrupts sleeping in the patient, comprising the steps of:
   (a) providing a continuous positive airway pressure machine having an air flow pressure control device accessible by the patient during use of said continuous positive airway pressure machine, a face attachment for attaching to the face of the patient, and a hose attached at a first end to said continuous positive airway pressure machine and at a second end to said face attachment, wherein said hose is operable to deliver continuous positive air flow pressure from said continuous positive airway pressure machine directly to said face attachment;
   (b) attaching said face attachment to the face of the patient;
   (c) activating said continuous positive airway pressure machine to produce a continuous positive airway pressure in the lungs of the patient; and
   (d) adjusting the continuous positive airway pressure by adjusting said air flow pressure control device to a level at which the patient feels that the pain produced by breathing in and out is reduced or eliminated and thereby preventing interruption of sleep caused by the pain, wherein said adjusting said air flow pressure control device is manually performed by the patient during use of said continuous positive airway pressure machine.

2. The method according to claim 1, further comprising the step of repeating steps (a) through (d) until no movement of the one or more fractured ribs is felt by the patient during breathing in and out when the patient is not using said continuous positive airway pressure machine.

\* \* \* \* \*